United States Patent
Calvert (10) Patent No.: US 10,532,164 B2
(45) Date of Patent: Jan. 14, 2020

(54) RETRACTABLE NEEDLE ASSEMBLIES

(71) Applicant: Owen Mumford Limited, Oxford (GB)

(72) Inventor: Jack Calvert, Oxford (GB)

(73) Assignee: Owen Mumford Limited, Oxford (GB)

( * ) Notice: Subject to any disclaimer, the term of this patent is extended or adjusted under 35 U.S.C. 154(b) by 166 days.

(21) Appl. No.: 15/531,678

(22) PCT Filed: Nov. 27, 2015

(86) PCT No.: PCT/GB2015/053632
§ 371 (c)(1),
(2) Date: May 30, 2017

(87) PCT Pub. No.: WO2016/083834
PCT Pub. Date: Jun. 2, 2016

(65) Prior Publication Data
US 2018/0280627 A1    Oct. 4, 2018

(30) Foreign Application Priority Data
Nov. 28, 2014 (GB) .................................. 1421212.0

(51) Int. Cl.
*A61M 5/32* (2006.01)
(52) U.S. Cl.
CPC ........ *A61M 5/3221* (2013.01); *A61M 5/3257* (2013.01); *A61M 5/3278* (2013.01);
(Continued)
(58) Field of Classification Search
CPC .. A61M 5/322; A61M 5/3221; A61M 5/3257; A61M 5/3278
See application file for complete search history.

(56) References Cited

U.S. PATENT DOCUMENTS

| 5,084,019 A | 1/1992 | Gartz |
| 5,891,093 A | 4/1999 | Dysarz |

(Continued)

FOREIGN PATENT DOCUMENTS

| CN | 1531446 | 9/2004 |
| EP | 1712779 A2 | 10/2006 |

(Continued)

OTHER PUBLICATIONS

International Search Report and Written Opinion dated Mar. 21, 2016, International Application No. PCT/GB2015/053632, 9 pages.

(Continued)

*Primary Examiner* — Nathan R Price
*Assistant Examiner* — Melissa A Snyder
(74) *Attorney, Agent, or Firm* — Quarles & Brady LLP (57) ABSTRACT

A retractable needle assembly (1) is disclosed comprising a body portion (10); a needle (50) having a forward end (52) and being movable between an operable orientation in which the forward end projects forwardly from the body portion, and a safe orientation in which said forward end (52) is retracted into the body portion (50). The needle assembly further comprises a deflector (70) mounted in the body portion (50), which is moveable between a first position and a second position, wherein the movement of the deflector (70) between its first and second position urges the needle into its safe orientation, the deflector being biased towards the second position; a latching mechanism which holds the deflector in the first position; and an actuator (90), operable to release the latching mechanism.

12 Claims, 5 Drawing Sheets

(52) U.S. Cl.
CPC ............... *A61M 2005/3228* (2013.01); *A61M 2005/3284* (2013.01)

(56) References Cited

U.S. PATENT DOCUMENTS

| | | | |
|---|---|---|---|
| 5,935,113 A | 8/1999 | Dysarz | |
| 6,186,979 B1 * | 2/2001 | Dysarz | ............... A61M 5/3278 128/898 |
| 2002/0068909 A1 | 6/2002 | Alchas et al. | |

FOREIGN PATENT DOCUMENTS

| | | | | |
|---|---|---|---|---|
| EP | 2574359 A1 * | 4/2013 | .......... | A61M 5/3257 |
| EP | 2574359 A1 | 4/2013 | | |
| WO | 0056384 A1 | 9/2000 | | |

OTHER PUBLICATIONS

GB Search Report dated May 7, 2015, United Kingdom Application No. GB1421212, 3 pages.

* cited by examiner

RETRACTABLE NEEDLE ASSEMBLIES

CROSS-REFERENCE TO RELATED APPLICATIONS

This application represents the U.S. National Stage of International Application No. PCT/GB2015/053632 filed on Nov. 27, 2015, which is incorporated by reference in its entirety, and is based upon, claims priority to, and incorporates herein by reference in its entirety, United Kingdom Patent Application Serial No. GB 1421212.0, filed Nov. 28, 2014.

FIELD OF THE INVENTION

This invention relates to retractable needle assemblies for attachment to, or forming an integral part of, a syringe or cartridge arrangement or other injection device.

BACKGROUND OF THE INVENTION

There are many situations in which an injection needle is required to be shielded after use to prevent the risk of needle stick injury. This applies not only to single use devices such as disposable syringes and the like, but also to multiple use devices such as cartridges where a disposable needle is secured, e.g. by screwing or other suitable connection action, into a cartridge or adaptor and replaced for each subsequent injection. This is especially important in clinics and hospitals where the user is injected by a clinician, where the risk of cross-infection is greater.

U.S. Pat. No. 5,476,106 discloses an arrangement in which a cannula extends diametrically through a reel mounted in housing. The reel may be rotated by means of a flat twist handle that is coplanar with the axis of the cannula and rotates about an axis in the same plane. In order to destroy the cannula after use the twist handle is twisted around its axis several times to wind the cannula around the reel and to draw it into the housing.

A problem with this arrangement is that it encourages two-handed use by the user holding the medical instrument in one hand and twisting the twist handle by several revolutions with the other. When grabbing the twist handle, the user is likely to approach it from the front or side, thus increasing the risk of inadvertent needle stick injury. Also, the user will need to grip and release the twist handle several times when retracting the cannula and thus increases the likelihood of an accidental needle stick injury. The manual winding of the lever to retract the needle to a safe position takes some time. Manual effort and dexterity on the part of the user is necessary which might be particularly difficult for people with limited strength and/or movement.

Embodiments of the invention seek to provide retractable needle assemblies which overcome some or all of these problems.

SUMMARY OF THE INVENTION

Accordingly, in one aspect, this invention provides a retractable needle assembly comprising: a body portion; a needle having a forward end and being movable between an operable orientation in which the forward end projects forwardly from the body portion, and a safe orientation in which the forward end is retracted into the body portion; a deflector mounted in the body portion, which is moveable between a first position and a second position, wherein the movement of the deflector between its first and second position urges the needle into its safe orientation, the deflector being biased towards the second position; a latching mechanism which holds the deflector in the first position; and an actuator, operable to release the latching mechanism.

The term forward end of the needle it is intended to include a section of the needle body as well as the needle tip. This section of the needle may also be referred to as the forward portion of the needle.

When the needle is in the safe orientation in which the forward end of the needle is retracted into the body portion, the retracted section of needle may be deflected or permanently deformed. Thus it will be appreciated that the deflector may be arranged to deform the needle during movement from its first to second position.

The latching mechanism may include at least two cooperating features. The cooperating features may include complementary engagement features which engage hold the deflector in its first position, thereby prevent the deflector moving.

When the needle is in its safe position, the forward end may be retracted into the body portion. When the forward end of the needle is retracted into the body portion, it may be deflected or permanently deformed.

An intermediate portion of the needle may extend through the deflector and the deflector may be rotatable in the body portion between the first and the second position in order to angularly displace the intermediate portion of the needle. The intermediate portion of the needle may be locked, glued or otherwise secured in the deflector. The intermediate portion of the needle may pass through a central bore in the deflector and may be locked, glued or otherwise secured in the deflector bore.

The deflector may be clicked or snap-fitted into the body portion and may also be retained in the body portion against removal. The deflector may, therefore, be moveably retained in the body portion.

The retractable needle assembly may also include a resilient element, for example a spring, which biases the deflector in its second position. The spring may be a torsion spring. The spring may have a first end coupled to the deflector. The second end of the spring may be coupled to the body portion.

The latching mechanism may include at least one latching element, and at least one locking feature, for example a locking surface, which is configured to engage the latching element thereby holding the deflector in its first position.

The actuator may be operable to unlock or disengage the cooperating features. The actuator may be operable to disengage the complementary engagement features. The actuator may be operable to move the latching element out of engagement with the locking feature.

The at least one latching element may provided on one of the deflector and the actuator. The at least one locking surface may be provided on the other of the deflector and the actuator. The locking surface may be provided on the actuator. The latching element may be provided on the deflector.

The actuator may be urged into the body or pressed perpendicularly to the rotation axis to disengage the cooperating features. The actuator may be urged into the body or pressed perpendicularly to the rotation axis to move the latching element and the locking feature out of interlocking alignment. The actuator may be provided with an annular channel into which the latching element moves and in which it is free to move rotationally.

The actuator may be provided with engagement features which engage with internal features in the main body portion when the actuator is mounted in the recess to lock the actuator against rotational movement. The actuator may be provided with engagement features which engage with internal features in the main body recess when the actuator is mounted in the recess to lock the actuator against rotational movement. The actuator and the recess may be provided with cooperating features which are configured to engage when the actuator is mounted in the recess to prevent rotational movement of the actuator in the recess. The actuator may be provided with radially extending projections. The inner wall of the recess may be provided with corresponding inward protrusions, which are configured to engage with the actuator radial projections when the actuator is mounted in the recess to prevent rotational movement of the actuator in the recess.

The needle may be a single ended needle with an exposed patient end that is retracted by operation of said deflector element. Alternatively, the needle may be double ended with a rear end opposite the patient end configured in use for piercing a seal element. In this instance the deflector element may cause both ends of the needle to retract into the body portion upon rotation thereof. The deflector may cause both ends of the needle to wrap around the deflector upon rotation thereof. The ends of the needle may wrap around the periphery of the deflector.

Alternatively, the rear end may be fixed, with the deflector element causing the only forward end of the needle to retract.

The intermediate portion of the needle may extend through the body portion along a longitudinal needle axis, and the deflector may slideable in the body portion in a direction perpendicular to the needle axis to laterally displace the intermediate portion of the needle.

The latching mechanism may include at least two cooperating features, including complementary engagement features which engage to prevent the deflector sliding and hold the deflector in its first position.

An intermediate portion of the needle may extend through the deflector and the deflector may be slidable in the body portion between the first and the second position in order to laterally displace the intermediate portion of the needle. The intermediate portion of the needle may be locked, glued or otherwise secured in the deflector. The intermediate portion of the needle may be pass through a bore in the deflector and may be locked, glued or otherwise secured in the deflector bore.

The resilient element may exert a force on the deflector in a direction perpendicular to the needle axis to bias the deflector to its second position. The resilient element may be a spring. The spring may be a tension spring, a compression spring or any other suitable resilient member which exerts a force on the deflector urging it to its second position.

The latching mechanism may include at least one latching element, and may further include at least one locking feature, for example a locking surface, which is configured to engage the latching element to hold the deflector in its first position.

The latching mechanism may include at least two cooperating features. The cooperating features may include complementary engagement features which engage to prevent the deflector sliding and hold the deflector in its first position. The actuator may be operable to move the latching element out of engagement with the locking feature. The actuator may be urged into the body or pressed perpendicularly to the needle axis to disengage the cooperating features.

The at least one latching element may be provided on one of the deflector and the actuator. The at least one locking feature may be provided on the other of the deflector and the actuator.

The deflector element may cause both ends of the needle to retract into the body portion as it moves to its second position. The deflector element may cause both ends of the needle to wrap around the deflector as it moves into its second position. The ends of the needle may wrap around the periphery of the deflector.

A rear portion of the body portion may comprise a connection mechanism for connecting the needle assembly to a syringe, cartridge or other injection device. The connection mechanism may be a threaded portion, bayonet fitting or any other suitable engagement element which corresponds to the engagement element on the injection device.

The retractable needle assembly may also include a safety mechanism to prevent accidental operation of the actuator, wherein the safety mechanism can be deactivated by a user. The safety mechanism may hold the assembly in the first, pre-injection position to prevent inadvertent firing of the device. The safety mechanism can prevent the actuator from being operated unintentionally, or in other words it ensures that the latching mechanism cannot be released accidentally. The safety mechanism can prevent the actuator from depressed, slid or otherwise operated. The safety mechanism may be an active safety mechanism and may be configured such that the user can deactivate or remove it prior to injection.

A retractable needle assembly according to any of the previous claims, further comprising a removable protector which shields or covers the forward end of the needle, and may also shield or cover at least a part of the forward portion of the needle assembly. The retractable needle assembly can be provided with a pre-injection protector, such as a container, needle shield or sheath, or any other well-known form of protection, which protects the user from accidental harm when handling the needle assembly before injection. The protector can be provided to shield or cover the forward end of the needle, and it may also shield or cover at least a part of the forward portion of the needle assembly.

The safety mechanism may be incorporated with or provided as part of the removable protector.

Whilst the invention has been described above, it extends to any inventive combination of the features set out in the following description or claims or drawings.

The embodiments illustrated in the Figures are needle assemblies intended to be screwed or otherwise attached to the forward end of a syringe, cartridge or injection device to allow injection of a substance.

DESCRIPTION OF AN EMBODIMENT

In the following embodiments, the terms "forward" and "front" refer to the patient end of the needle assembly or component thereof, and the term "rear" refers to the non-patient end of the needle assembly or component thereof. In other words, the term "rear" means distant or remote from the injection site during use.

Figure 1:
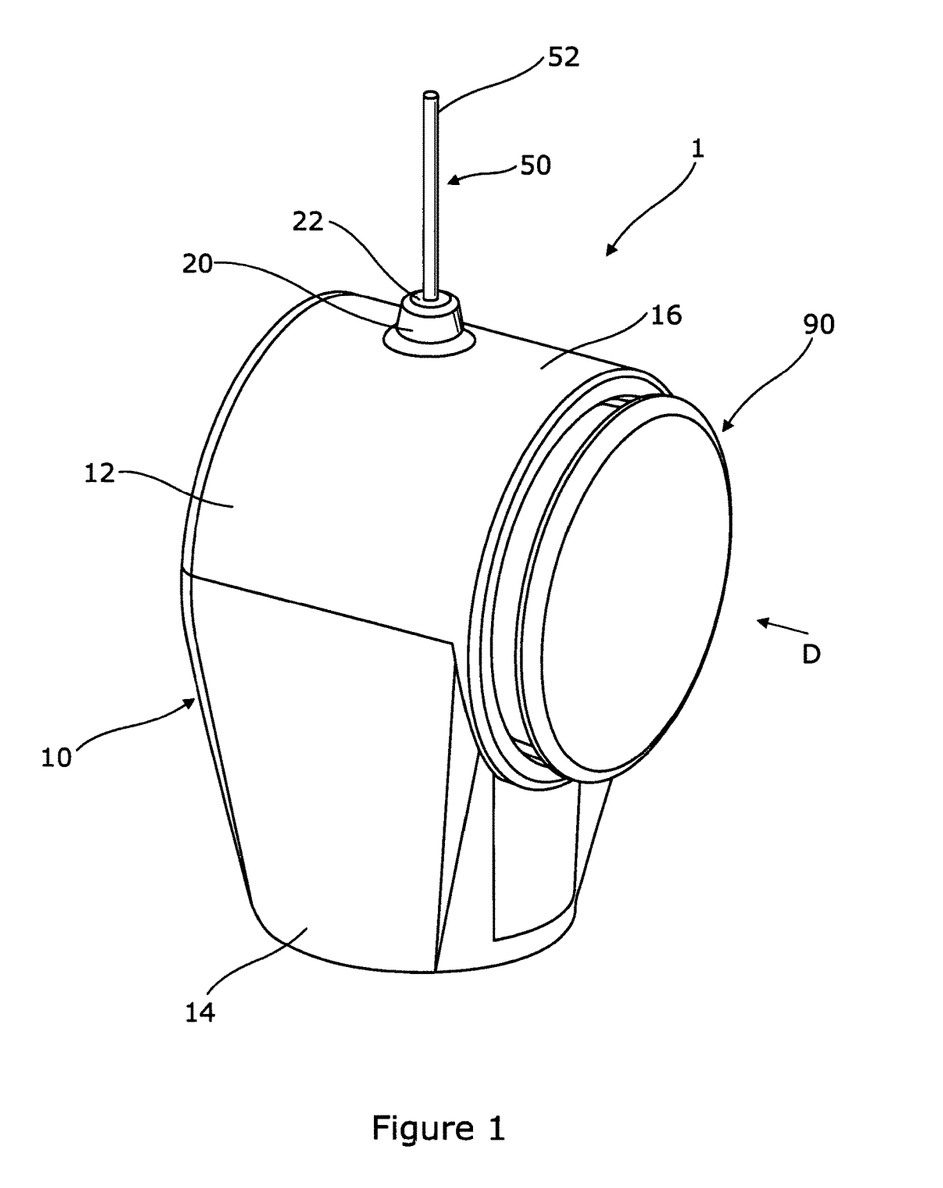
FIG. 1 shows a perspective view of a first retractable needle assembly in accordance with an embodiment of the invention in a first position with the needle in an operable orientation, in an exposed condition ready to deliver an injection.

FIG. 1 shows a retractable needle assembly 1 according to an embodiment of the invention in a first position, which is the configuration of the assembly before and during injection. The retractable needle assembly 1 includes a main body 10, a needle 50, a deflector in the form of a hub 70, a torsion spring 60 and an actuator 90.

The main body 10 a main housing portion 12; a rear portion 14; and a forward portion 16. The main housing portion 12 includes a recess 30 on a first side 2 of the needle assembly 1.

A forward guide portion 20 extends from a front surface of the forward portion 16, the forward guide portion 20 having a central through-hole or forward bore 22, through which the needle 50, having a forward end 52 with a tip, extends.

The actuator or button 90 is provided on the first side 2 of the needle assembly 1and is mounted in the recess 30. The actuator 90 includes inner and middle parts (not shown in FIG. 1) which are located within the main body 10, and an outer part 96 which extends out of the recess 30. The actuator 90 is operable in a direction D, which is generally perpendicular to the needle axis.

Figure 2:
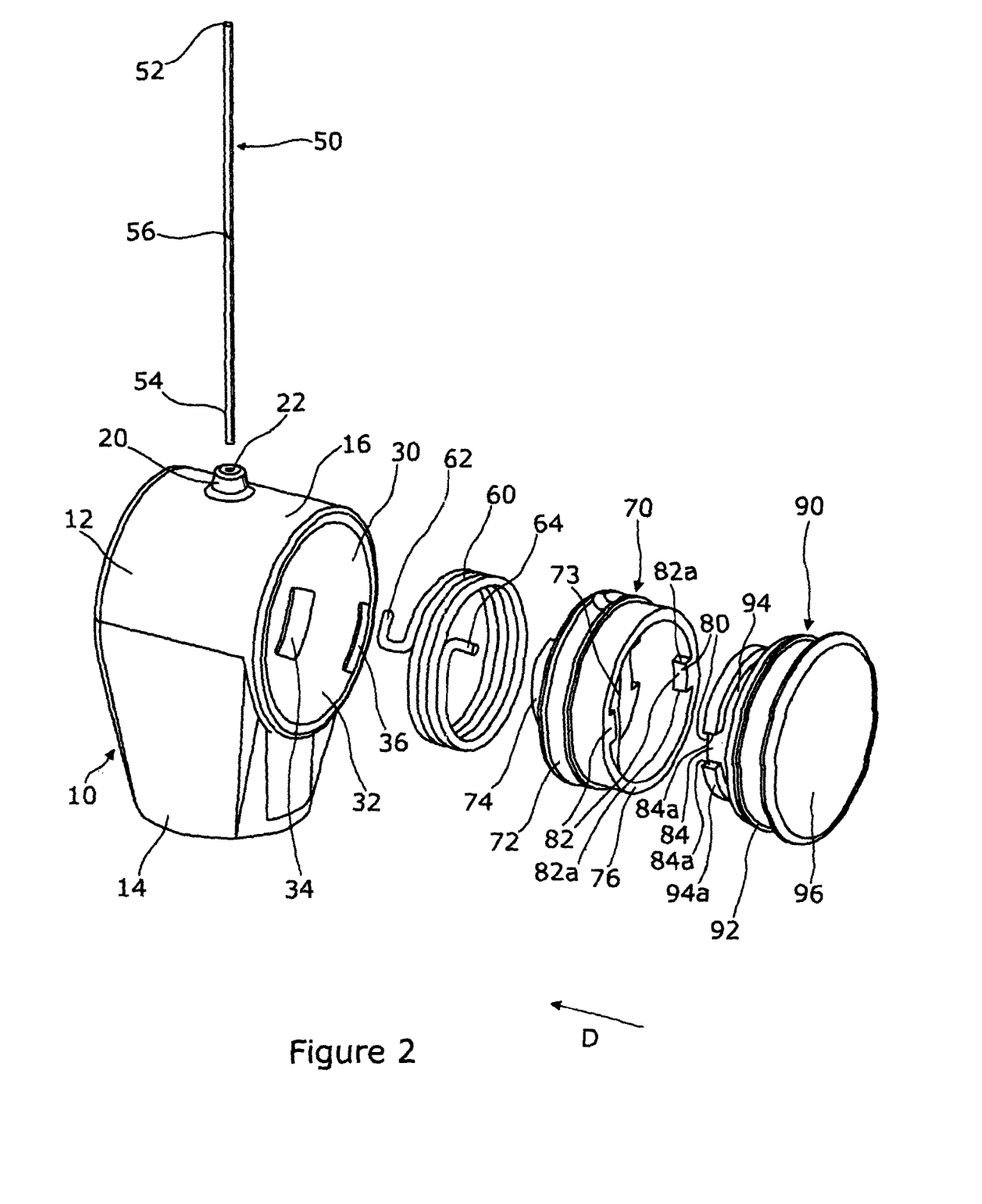
FIG. 2 shows a perspective exploded view of the retractable needle assembly of FIG. 1 in the first position.

Referring now to FIG. 2, which shows an exploded view of the components of the retractable needle assembly 1, the rear portion 14 includes an internal threaded bore 18 configured to be threaded onto the forward end of a syringe or cartridge (not shown) to connect the needle assembly 1 to the syringe or cartridge.

The recess 30 extends into the main housing portion 12, and has a substantially cylindrical configuration with a central axis A. The recess 30 includes a side wall 32 having at least one inward projection 34. In this embodiment, three equally circumferentially spaced, inward projections 34 are provided. However, alternatively, one, two, four or any other suitable number of inward projections or projecting elements can be provided on the side wall 32. The recess 30 includes at least one lip element 36 at the outer edge of the inner wall 32. In this embodiment, three equally spaced lip elements 36 are provided. However, any suitable number of lip elements can be provided circumferentially around the outer edge of the inner wall.

The needle assembly 1 also includes a resilient element in the form of a torsion spring 60 mounted in the recess 30 and having a first (inner) end 62 which is arranged to engage the body 10.

The hub or drum 70 is rotatably mounted about the axis A within the recess 30. The spring 60 also has a second (outer) end 64 which engages with the hub 70. The hub 70 includes an essentially cylindrical central section 72; an inner portion 74 having a smaller diameter than the central section 72, and an outer portion 76. A central needle bore 73 extends diametrically through the central section 72. The outer portion 76 is provided with inwardly projecting elements 82. The projecting elements 82 have a thickness x in the axial direction A. In this embodiment, two diametrically opposite projecting elements are provided. However, alternatively, one, three, four or any other suitable number of projecting elements can be provided.

The needle 50 includes a forward end (or forward portion) 52, rear end (or rear portion) 54 and an intermediate portion 56. The retractable needle assembly 1 may be provided with a removable container, needle shield or sheath, or any other well-known form of removable protection (not shown in the Figures) which covers at least the forward end 52 to protect the user from accidental harm when handling the needle assembly before injection.

The actuator 90 is essentially cylindrical in shape having a middle part 92; an inner part 94 with a smaller diameter than the middle part 92; and an outer part 96. The inner part 94 is provided with an outwardly extending annular section 94a having cut-outs 84. The outwardly extending section 94a has a thickness in the axial direction A which approximately corresponds to the thickness x of the projecting elements 82. In this embodiment two diametrically opposite cut-outs 84 are provided which correspond to the two projecting elements 82. However, an alternative number of cut-outs could be provided depending on the number of projecting elements.

In this embodiment, the actuator 90 is provided with radially projecting features on its outer surface (not shown in the Figures) which cooperate with corresponding protrusions provided on the inner wall of the recess 30 to lock the actuator 90 against rotational movement in the recess 30, thereby preventing rotational movement of the actuator 90 in the recess 30 when the actuator is fully mounted in the recess.

FIGS. 3A to 3D show the needle assembly 1 in the first position with the needle 50 in an exposed condition ready to deliver an injection.

The second side 4 of the main housing portion 12, opposite to the actuator 90, includes a second substantially cylindrical recess 40. The second recess 40 is co-axial with the first recess 40, and has a diameter d2 which is smaller than the diameter d1 of the first recess 30. The second recess 40 provides a cylindrical side wall 42 which supports the spring 60 and hub 70 (as explained below).

The spring 60 is located in the first recess 30 and in its mounted configuration; the spring 60 extends around second recess, i.e. outside the side wall 42. A first end 62 of the spring 60 is secured internally within the recess 30. The hub 70 is mounted in the recess 30, with the inner end 72 extending within the spring 60. A second end 64 of the spring engages with the hub 70. In the first position, the spring 60 is pre-loaded and biases the hub 70 to rotate in a counter-clockwise direction, when viewed from the first side 2 of the main body 10. In other words, the spring 60 biases the hub 70 towards a second, post-injection or disposal position, which is explained further below.

The central needle bore 73 of the hub 70 is aligned with both the forward needle bore 22 and a rear needle bore 24 provided in the rear portion 14 of the main body 10 (such that the bore may together receive the needle 50). The hub 70 is provided with an outward radial protrusion 76. In this embodiment, the radial protrusion 76 extends around the circumference of the hub 70 in a substantially annular shape.

Each inward projection 34 on the inner wall 32 has a first sloped surface 34a facing towards the first side 2; and a second surface 34b. As the hub 70 is inserted into the recess 30 in the insertion direction D, the protrusion 76 slides along the first surface 34a and passes over the inward projections 34. Thus, the hub 70 may be snap-fitted into the housing and the second surface 34b is configured to engage with the protrusion 76 to limit axial movement of the hub 70 in a direction opposite to the insertion direction D. In this embodiment, the second side 34b is formed substantially perpendicular to the side wall 32. This arrangement ensures that the hub 70 is correctly positioned; ensuring that the central bore 73 is aligned with the bores 22, 24 in the main body 10.

Figure 3A:
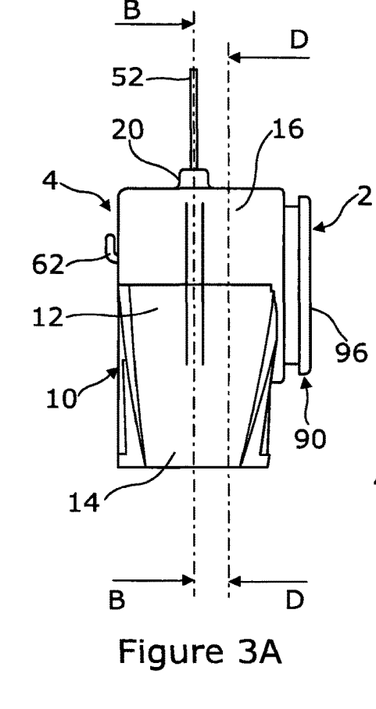
FIG. 3A shows a side view of the retractable needle assembly of FIG. 1.
Figure 3B:
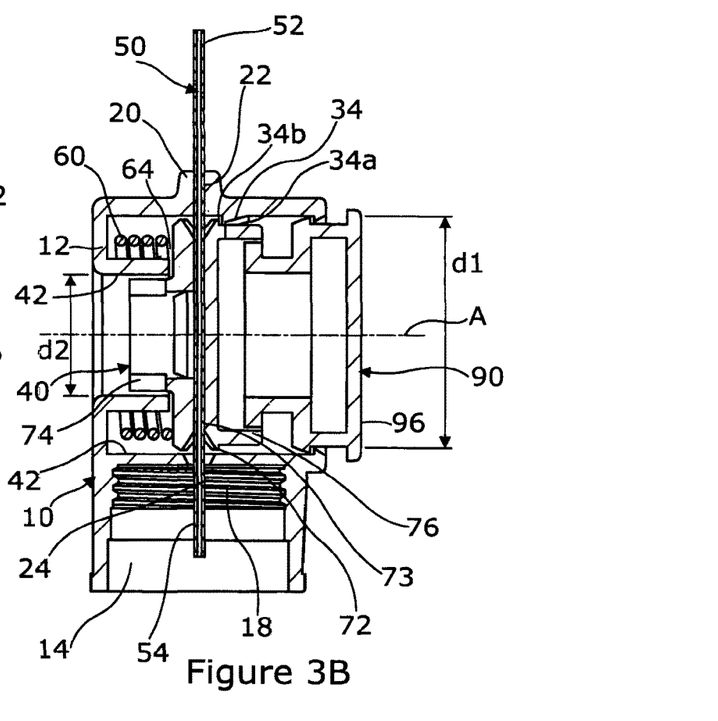
FIG. 3B shows a cross-sectional side view of the retractable needle assembly of FIG. 3A.
Figure 3C:
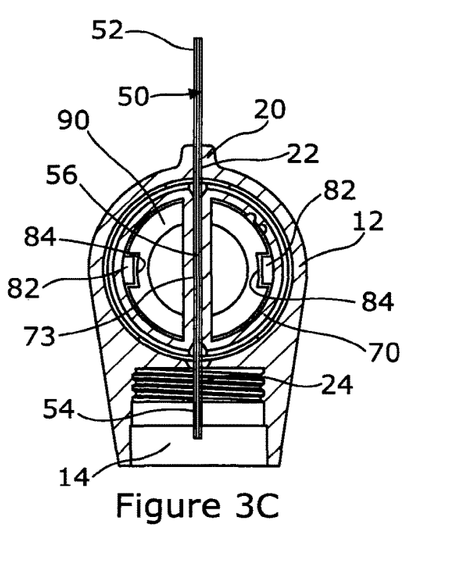
FIGS. 3C and 3D show cross-sections B-B and D-D as indicated in FIG. 3A.
Figure 3D:
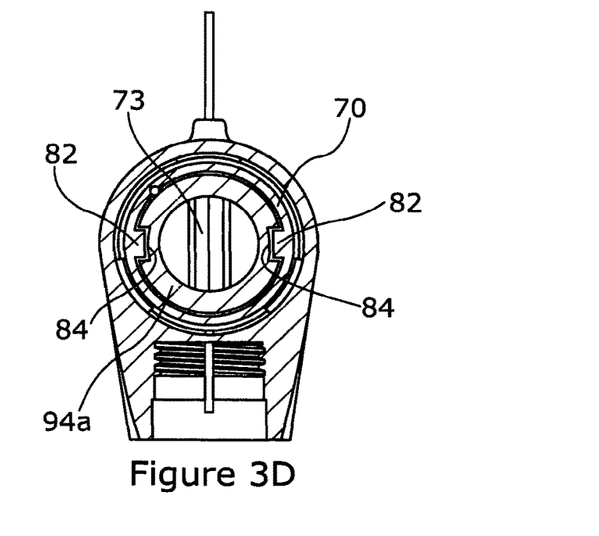

As shown in FIGS. 3B and 3C, the needle 50 is inserted through the forward needle bore 22, so that the front end 52 extends forwardly from the guide portion 20, the intermediate portion 56 is located within the central needle bore 73, and the rear portion 54 extends rearwardly from the rear needle bore 24. The intermediate portion 56 is locked or secured in the central needle bore 73 of the hub 70.

The inner section 94 of the actuator 90 extends within the outer section 76 of the hub 70. Each cut-out 84 is configured to receive and engage a corresponding projecting element 82 on the hub 70. In the first position, the two cut-outs 84 are aligned with the two projecting elements 82 (see FIG. 3D). The projecting element surfaces 82a engage and contact against the annular ring surfaces 84a. This means that the cut-outs 84 act as locking surfaces which hold the projecting elements 82, the elements 82 acting as latching elements cooperating with the locking surfaces. Since the projecting elements 82 are locked or restrained, the hub 70 is prevented from rotating. The projecting elements 82 and cut-outs 84 therefore form locking surfaces and latching elements of a latching mechanism 80 which holds the retractable needle assembly 1 in the first position against the force of the spring 60. In the first position, the needle assembly 1 can be used with a syringe or cartridge to inject a medicament.

FIGS. 4A to 4D show the needle assembly 1 in the second position with the needle 50 retracted in a safe configuration.

Figure 4A:
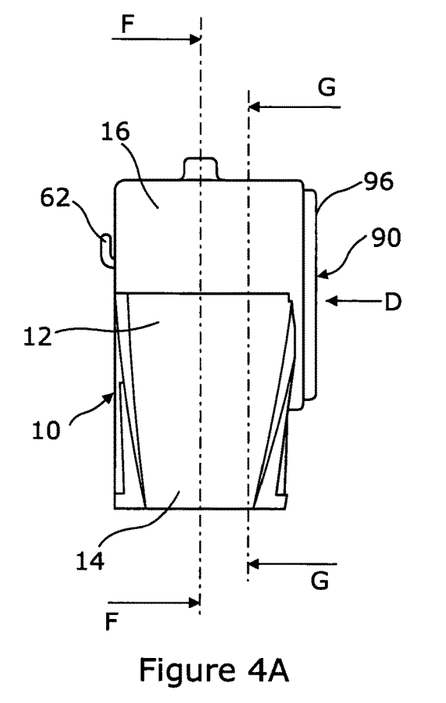
FIG. 4A shows a side view of the first retractable needle assembly in a second position with the needle in a safe orientation, in the retracted position.
Figure 4B:
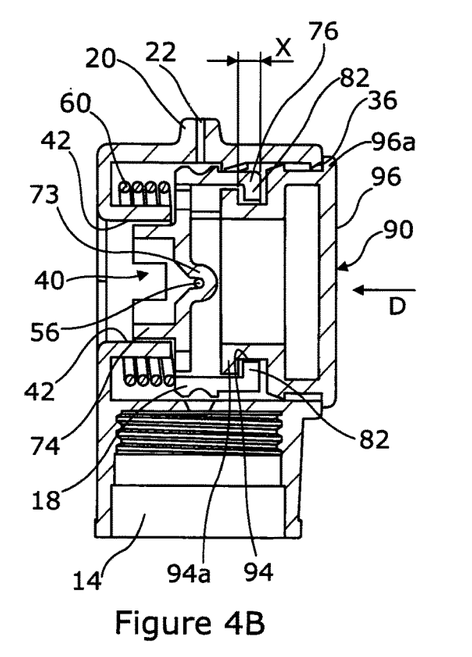
FIG. 4B shows a cross-sectional side view of the assembly of FIG. 43A.

When it is required to retract the needle 50, for example following an injection and dispensing of the medicament from the syringe or cartridge, the operator presses outer part 96 of the actuator 90 in the direction D. The actuator 90 moves inwardly within the recess 30 relative to both the main body 10 and the hub 70, by at least a distance x to a second position, as shown in FIGS. 4A and 4B. In this embodiment, the outer external edge 96a of the actuator contacts with the main body portion 112, and further axial movement is prevented by the lip elements 36.

Figure 4C:
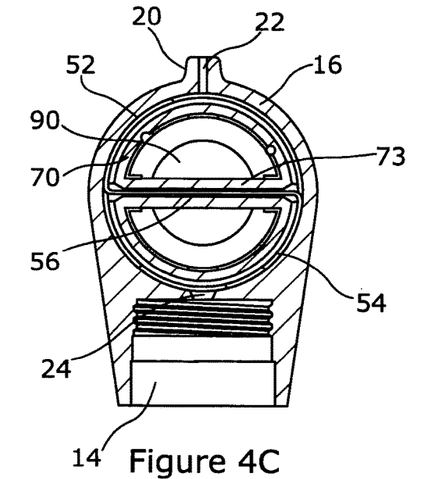
FIGS. 4C and 4D show views through the cross-sections F-F and G-G as indicated in FIG. 4A.
Figure 4D:
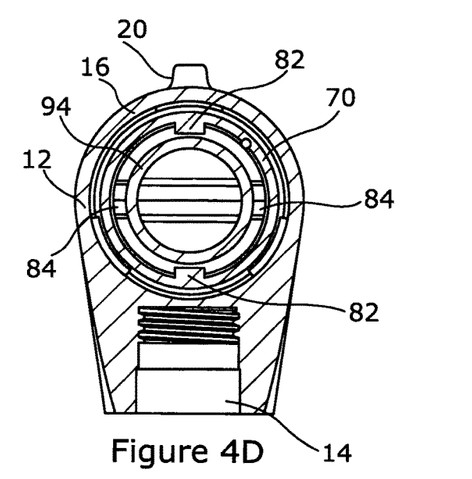

As the actuator 90 moves into the recess 30, the cut-outs move 84 axially away from and out of alignment with the projecting elements 84, and the projecting elements 82 become aligned with the reduced diameter section 94a of the actuator (FIGS. 4B and 4D). In this configuration, the projecting elements 82 do not contact with the actuator 90 which means that the hub 70 is no longer restrained or locked against rotational movement. In other words, the latching mechanism is released. This means that the hub 70 rotates due to the biasing force of the spring 60. The reduced diameter section 94a provides an annular groove, or channel, in which the projecting members 82 may run during rotation of the hub 70 relative to the actuator 90. As the hub 70 rotates, the intermediate portion 56 of the needle 50 is rotated which causes the forward end 52 and rear end 54 of the needle to be wrapped around the periphery of the hub 70, as shown in FIG. 4C.

Both the forward end 52 and rearward end 54 of the needle are retracted inside of the main body 10 and there is no risk of accidental needle stick injury for the user. The user is then able to safely remove the needle assembly from the injection device and dispose of it.

In another embodiment (not shown in the Figures, the engagement surfaces 82a on the hub projecting element 82 are angled or sloped surfaces. The two sloped surfaces 82a on each element are configured to slope in a diverging manner in the direction into the recess (indicated with arrow D in FIG. 2). The corresponding engagement surfaces 84a on the annular ring 84 are also angled or sloped in the same manner.

The effect of the sloped surfaces 82a and 84a is that as the hub attempts to rotate under pressure of torsion spring, the angled surface contacts with actuator and cam the actuator out towards locking elements provided on the outer periphery of the recess (not shown) which lock it into the recess. In other words the torsion spring and the angled surfaces on the hub work push the actuator outwards, but the actuator is retained in the recess by the locking elements. The locking elements have a sloped or forward angled surface which faces outward from the recess and a rear surface with a stepped or barbed profile. This means when the actuator is mounted into the recess the outer edges move over the sloped surfaces. When the actuator 90 is pressed, the hub projecting element angled surfaces rotate the hub 70 slightly against the torsion spring force direction until the actuator 90 is far enough forward that the hub projecting elements 82 can run freely in the actuator channel 94a.

In other embodiments (not shown in the Figures), the actuator is provided in an alternative location on the main body and/or is operable in a different direction. For example, in one embodiment, the actuator is provided on the outer surface of the main body and moveable radially inwardly or outwardly with respect to the hub. In another embodiment, the actuator is provided on the outer surface of the main body and operable in the axial direction A.

Figure 5A:
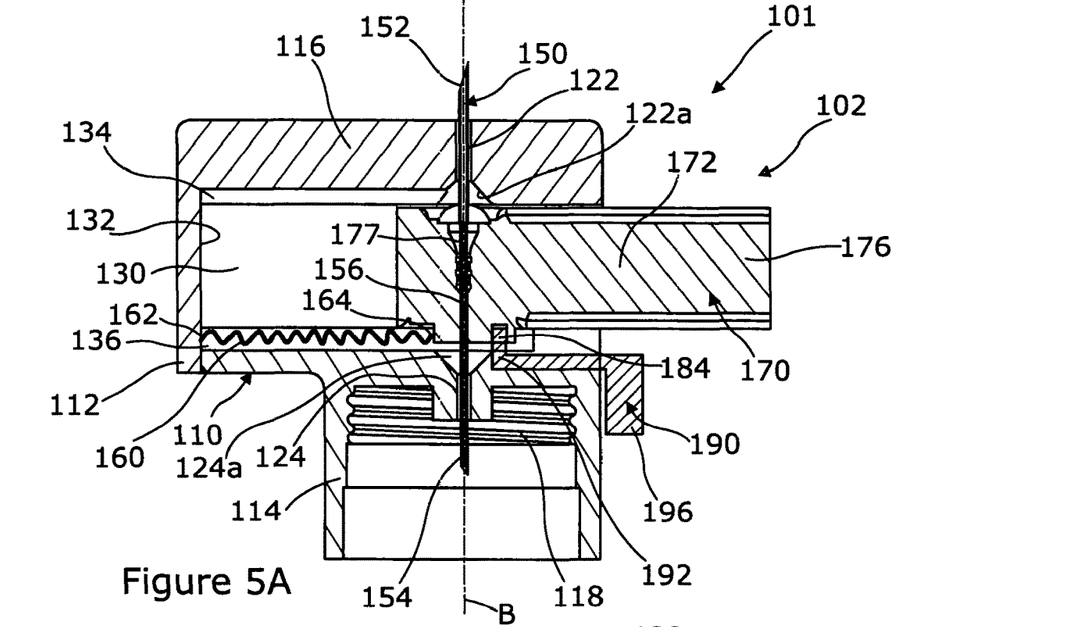
FIG. 5A shows a cross-sectional side view of a second retractable needle assembly in accordance with another embodiment of the invention, in a first position with the needle in an operable orientation, being exposed and ready to deliver an injection.
Figure 5B:
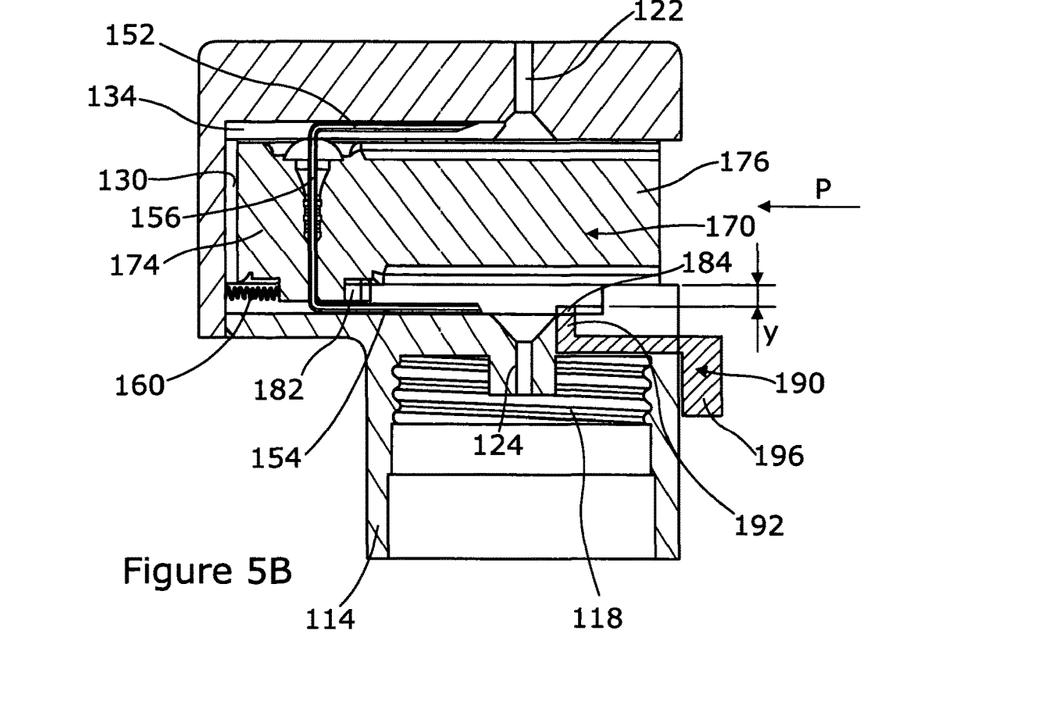
FIG. 5B shows a cross-sectional side view of the second retractable needle assembly, in a second position with the needle retracted in a safe orientation.

A second retractable needle assembly is shown in FIGS. 5A and 5B. In this arrangement, the retractable needle assembly 101 includes mechanism which deflects the needle 150 laterally or sideways in relation to a needle axis B to retract the forward end of the needle 150 into the needle assembly.

FIG. 5B shows the retractable needle assembly 101 in a first position with the needle 150 in an exposed condition ready to deliver an injection.

The retractable needle assembly 101 includes a main body 110, a needle 150, a deflector in the form of a slider 170, a tension spring and an actuator 190. The main body comprises a main housing portion 112; a rear portion 114 and a forward portion 116. The main housing portion 12 includes a recess 130 on a first side 102, which extends into the main housing portion 112. The recess 130 includes an inner end wall 132; and groves 134 and 136 on the forward and rear inner walls which are aligned with the conical entrances 122a and 124a.

The forward portion 116 includes a through-hole or forward needle bore 122 extending from the forward surface to the recess 130, having a conical entrance 122a at the recess 130. The portion 114 includes an internal threaded bore 118 configured to be threaded onto the forward end of a syringe or cartridge (not shown) to connect the needle assembly 101 to the syringe or cartridge. The rear portion 114 includes a through-hole or rear needle bore 124 extending rearwardly from the recess 130, having a conical entrance 124a at the recess 130.

The slider 170 is mounted for sliding movement in the recess 130. The slider 170 includes an inner portion 174; an outer portion 176 and a central portion 172. In the first position shown in FIG. 5A, the outer portion 176 and the central portion 172 are located outside the main body 110. The slider 170 includes a through hole or needle bore 177 which in the first position is aligned with the forward needle bore 122 and the rear needle bore 124.

The needle 150 extends along the axis B, and includes a forward end 152, rear end 154 and an intermediate portion 156. In the first position the forward end 152 extends forwardly from the needle assembly, and the needle 150 passes through the forward bore 122, through the slider bore 177 in which it is bonded or secured, and then through the rear bore 124.

The retractable needle assembly 101 may be provided with a removable container, needle shield or sheath, or any other well-known form of protection (not shown in the Figures) which covers at least the forward end 152 to protect the user from accidental harm when handling the needle assembly 101 before injection.

The retractable needle assembly 101 includes a resilient member in the form of a tension spring 160. A first end 162 of the tension spring is secured to the inner wall 132 of the recess 130 and a second end 164 of the tension spring is secured to the slider 170. The tension spring 160 biases the slider towards the inner wall 132. In a further embodiment (not shown), two tension springs are provided, and both springs are secured at one end to the inner wall and at the other end to the slider to bias the slider to its second position.

The actuator 190 is provided having a first end 192 which is located inside the main body and an outer end 106 which extends outside the main body 110. The first end 192 includes a projection 184. The slider 170 includes a recess 182. In the first position, the projection 184 is located within the recess 182 (see FIG. 5A). This means that the recess 182 acts as a locking surface which holds the projection 184. Therefore, the projection is a latching element. Since the projection 184 is locked or restrained, the slider 170 is prevented from moving or sliding laterally or sideways with respect to the needle axis B. This means that the recess 182 and the projection 184 form a latching mechanism 180. which holds the retractable needle assembly 101 in the first position against the force of the spring 160. In the first position, the needle assembly 101 can be used with a syringe or cartridge to inject a medicament.

In alternative embodiments, not show, the latching mechanism is be formed with two or more latching elements and two or more corresponding locking surfaces, or in other words with two or more cooperating projections and recesses.

In alternative embodiments, not shown, the actuator is be provided in a different part of the main body, and/or is operable in a different direction to unlock or release the deflector from its first position.

FIG. 5B shows the second retractable needle assembly 101 in its second position with the needle 150 retracted in a safe configuration.

When it is required to retract the needle 150, for example following an injection and dispensing of the medicament from the syringe or cartridge, the operator presses or slides the outer part 196 of the actuator 190 in the direction P. The actuator 190 moves rearwardly by at least a distance y to a rearward location, as shown in FIG. 5B. When the actuator 190 is in its rearward configuration, the projection 184 moves out of the recess 182 which means that the slider 170 is no longer restrained or locked against lateral movement. Therefore, the slider 170 moves to the second position, towards the inner wall 132 due to the biasing force of the spring 160, and the intermediate portion 156 of the needle 150 is forced sideward causing the forward end 152 and rear end 154 of the needle to be drawn into the grooves 134, 136, as shown in FIG. 5B. The forward end 152 and the rear end 154 of the needle are retracted inside of the main body 110 and there is no risk of accidental needle stick injury for the user.

If necessary, some form of latching arrangement may be provided to prevent disassembly of the slider from the body after it has moved to the second position.

In FIGS. 5A and 5B, the resilient element biasing the slider (deflector) towards the inner rear wall of the recess is a tension spring. In other embodiments (not shown), any other suitable resilient element is used to bias the slider in the same direction. For example, one or more compression springs are provided which act on the slider from the first side of the needle assembly to push the slider into the recess towards its second position.

In all embodiments of the invention, the needle assembly may also be provided with a safety mechanism (not shown) which holds the assembly in the first, pre-injection position to prevent inadvertent firing of the device. The safety mechanism prevents the actuator from being operated, or in other words it ensures that the latching mechanism cannot be released. The safety mechanism can be deactivated by the user prior to use. In the embodiments described above, the safety mechanism prevents the actuator from depressed, i.e. from being moved inwardly into the recess.

The invention claimed is:

1. A retractable needle assembly comprising:
   a body portion;
   a needle having a forward end and being movable between an operable orientation in which the forward end projects forwardly from the body portion, and a safe orientation in which said forward end is retracted into the body portion;
   a deflector mounted in the body portion, which is moveable between a first position and a second position, wherein movement of the deflector between the first position and the second position urges the needle into the safe orientation, the deflector being biased towards the second position, and wherein an intermediate portion of the needle extends through the deflector and the deflector is rotatable in the body portion between the first position and the second position in order to angularly displace the intermediate portion of the needle;
   a latching mechanism which holds the deflector in the first position, wherein the latching mechanism includes at least one latching element provided on the deflector, and at least one locking feature provided on the actuator which is configured to engage the latching element thereby holding the deflector in the first position; and
   an actuator, operable to release the latching mechanism, wherein, in use, the actuator is pressed perpendicularly to the needle axis to move the latching element out of engagement with the locking feature and into an annular channel provided on the actuator in which it is free to move rotationally.

2. The retractable needle assembly according to claim 1, wherein when the needle is in the safe orientation, the forward end is retracted into the body portion.

3. The retractable needle assembly according to claim 1, wherein the deflector is snap-fitted into the body portion and is retained therein against removal.

4. The retractable needle assembly according to claim 3 further including a resilient element which biases the deflector toward the second position.

5. The retractable needle assembly according to claim 4, wherein the resilient element is a torsion spring.

6. The retractable needle assembly according to claim 5, wherein the torsion spring has a first end coupled to the deflector, and a second end coupled to the body portion.

7. The retractable needle assembly according to claim 1, wherein the needle is double ended with a rear end opposite the forward end, the rear end being configured in use for piercing a seal element.

8. The retractable needle assembly according to claim 7, wherein the deflector causes both the forward end and the rear end of the needle to retract into the body portion upon rotation of the deflector.

9. The retractable needle assembly according to claim 7, wherein the rear end is fixed and the deflector causes only the forward end to retract.

10. A retractable needle assembly according to claim 1, wherein a rear portion of the body portion comprises a connection mechanism for connecting the needle assembly to a syringe, a cartridge, or another injection device.

11. A retractable needle assembly according to claim 1, further comprising a safety mechanism to prevent accidental operation of the actuator, wherein the safety mechanism can be deactivated by a user.

12. A retractable needle assembly according to claim 1, further comprising a removable protector which shields or covers the forward end of the needle, and is capable of shielding or covering at least a part of the forward portion of the needle assembly.

* * * * *